United States Patent
Bai et al.

(10) Patent No.: US 10,041,930 B2
(45) Date of Patent: Aug. 7, 2018

(54) TUNNELING JUNCTION TO DISTINGUISH TARGETED DNA SEGMENT

(71) Applicant: GLOBALFOUNDRIES INC., Grand Cayman (KY)

(72) Inventors: Jingwei Bai, Elmsford, NY (US); Niina S. Haiminen, White Plains, NY (US); Laxmi P. Parida, Mohegan Lake, NY (US); Gustavo A. Stolovitzky, Bronx, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 430 days.

(21) Appl. No.: 13/930,578

(22) Filed: Jun. 28, 2013

(65) Prior Publication Data

US 2015/0001079 A1 Jan. 1, 2015

(51) Int. Cl.
*G01N 33/487* (2006.01)
*B82Y 15/00* (2011.01)

(52) U.S. Cl.
CPC ........ *G01N 33/48721* (2013.01); *B82Y 15/00* (2013.01)

(58) Field of Classification Search
CPC ....... G01N 33/48721; G01N 33/48728; C12Q 1/6869; B82Y 5/00
See application file for complete search history.

(56) References Cited

U.S. PATENT DOCUMENTS

| 2003/0141189 | A1 | 7/2003 | Lee et al. |
| 2004/0149580 | A1* | 8/2004 | Flory ........................ B82Y 5/00 |
| | | | 204/518 |
| 2005/0136408 | A1 | 6/2005 | Tom-Moy et al. |
| 2006/0154399 | A1* | 7/2006 | Sauer ................... C12Q 1/6874 |
| | | | 438/48 |

(Continued)

FOREIGN PATENT DOCUMENTS

| EP | 1574837 A1 | 9/2005 |
| JP | 2005245369 A | 9/2005 |

(Continued)

OTHER PUBLICATIONS

Ohshiro, T., et al. "Tunnel-Current Based Single-Molecule Identification of DNA/RNA Oligmer by Using NANO-MCBJ" 2012 12th IEEE International Conference on Nanotechnology (IEEE-NANO). Aug. 2012. (2 pages).

(Continued)

*Primary Examiner* — Maris R Kessel
(74) *Attorney, Agent, or Firm* — David Cain; Hoffman Warnick LLC (57) ABSTRACT

A nanodevice includes a nanochannel disposed through a dielectric material. A first electrode is disposed on a first side of the nanochannel, is formed within the dielectric material and has a surface exposed within the nanochannel. A second electrode is disposed on a second side of the nanochannel, is formed within the dielectric material and has a surface exposed within the nanochannel opposite the first electrode. A power circuit is connected between the first and second (Continued)

electrodes to create a potential difference between the first and second electrodes such that portions of a molecule can be identified by a change in electrical properties across the first and second electrodes as the molecule passes.

19 Claims, 7 Drawing Sheets

(56) References Cited

U.S. PATENT DOCUMENTS

| | | | |
|---|---|---|---|
| 2007/0020146 A1* | 1/2007 | Young | B81C 1/00087 |
| | | | 422/82.01 |
| 2008/0171316 A1* | 7/2008 | Golovchenko et al. | 435/6 |
| 2008/0187915 A1* | 8/2008 | Polonsky | B82Y 15/00 |
| | | | 435/6.13 |
| 2010/0078325 A1* | 4/2010 | Oliver | G01N 33/48721 |
| | | | 204/452 |
| 2011/0236984 A1* | 9/2011 | Sun | C12Q 1/6869 |
| | | | 436/94 |
| 2012/0074925 A1 | 3/2012 | Oliver et al. | |
| 2012/0193231 A1 | 8/2012 | Afzali-Ardakani et al. | |
| 2012/0193237 A1* | 8/2012 | Afzali-Ardakani | B82Y 15/00 |
| | | | 204/627 |
| 2012/0288948 A1 | 11/2012 | Lindsay et al. | |
| 2013/0001082 A1 | 1/2013 | Afzali-Ardakani et al. | |

FOREIGN PATENT DOCUMENTS

| | | |
|---|---|---|
| WO | WO2012164679 A1 | 12/2012 |
| WO | WO2013011879 A1 | 1/2013 |

OTHER PUBLICATIONS

Zwolak, M., et al. "DNA Sequencing Via Electron Tunneling" IEEE International Symposium on Circuits and Systems. May 2012. pp. 2295-2298.

\* cited by examiner

TUNNELING JUNCTION TO DISTINGUISH TARGETED DNA SEGMENT

BACKGROUND

Technical Field

The present invention relates to nanodevices, and more particularly to devices and methods for analyzing genetic material strands.

Description of the Related Art

Current techniques for analyzing DNA strands employ optical detection with specially designed fluorescence marks. Such techniques incur high costs due the fluorescence molecules and suffer from low resolution due to optical limits. A cost-effective method with high resolution is thus in high demand to reduce the overall cost of the DNA sequencing and assembly.

SUMMARY

A nanodevice includes a nanochannel disposed through a dielectric material. A first electrode is disposed on a first side of the nanochannel, is formed within the dielectric material and has a surface exposed within the nanochannel. A second electrode is disposed on a second side of the nanochannel, is formed within the dielectric material and has a surface exposed within the nanochannel opposite the first electrode. A power circuit is connected between the first and second electrodes to create a potential difference between the first and second electrodes such that portions of a molecule can be identified by a change in electrical properties across the first and second electrodes as the molecule passes.

A nanodevice includes a nanochannel disposed through a dielectric material, a first electrode on a first side of the nanochannel formed within the dielectric material and having a surface exposed within the nanochannel and a second electrode on the first side of the nanochannel formed within the dielectric material and spaced apart by a gap from the first electrode by the dielectric material, the second electrode having a surface exposed within the nanochannel. A power circuit is connected between the first and second electrodes to create a potential difference between the first and second electrodes such that portions of a molecule can be identified by a change in electrical properties across the first and second electrodes as the molecule passes.

A method for analyzing a molecule includes providing a nanochannel disposed through a dielectric material, a first electrode formed within the dielectric material and having a surface exposed within the nanochannel, and a second electrode formed within the dielectric material and having a surface exposed within the nanochannel and a power circuit connected between the first and second electrodes to create a potential difference between the first and second electrodes such that portions of a molecule can be identified by a change in electrical properties across the first and second electrodes; feeding a linearized version of the molecule down the nanochannel such that the molecule passes between the first and second electrodes; and measuring the change in electrical properties across the first and second electrodes as the molecule is disposed between the first and second electrodes to characterize the molecule or portions thereof.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, nanodevices and methods for employing such devices are provided. In particularly useful embodiments, the nanodevices are employed to characterize, identify, analyze and/or assembly genetic material strands. In one embodiment, a deoxyribonucleic acid (DNA) molecule is passed through a nanodevice to detect regions that are double-stranded, and a distance between such regions. Distances are inferred from the timing between subsequent observations of double-stranded DNA. The nanodevice technology can be utilized, for example, by designing probes that bind to a specific DNA sequence, and then checking for the placement of those probes on the DNA molecule. The probes can be either plain single-stranded DNA sequences, or sequences with an indicator component attached, for distinguishing between different probes. The binding of a probe can be observed as a region of double-stranded DNA. The nanodevices enable the determination of a location of specific pre-defined probes, and estimate a distance between a pair of probes, in terms of number of base pairs.

Single strand or double strand DNA may be bound to probe molecules. The probe molecule includes a short single strand of DNA with a complimentary sequence for a part of interest of a targeted DNA sequence assembly. If the target DNA is single strand DNA, the probe or prober molecule can bind to the target DNA to make it partial double strand. The probe molecule can also include a mark molecule such as protein, conductive organic molecule, nanoparticles (e.g., metal, semiconductor), etc. to enhance a signal difference between a binding strand and non-binding strand. For double strand DNA, clip chemistry can be used to insert the probe molecule.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Designs for nanodevices may be included on an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of nanodevices on, e.g., integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
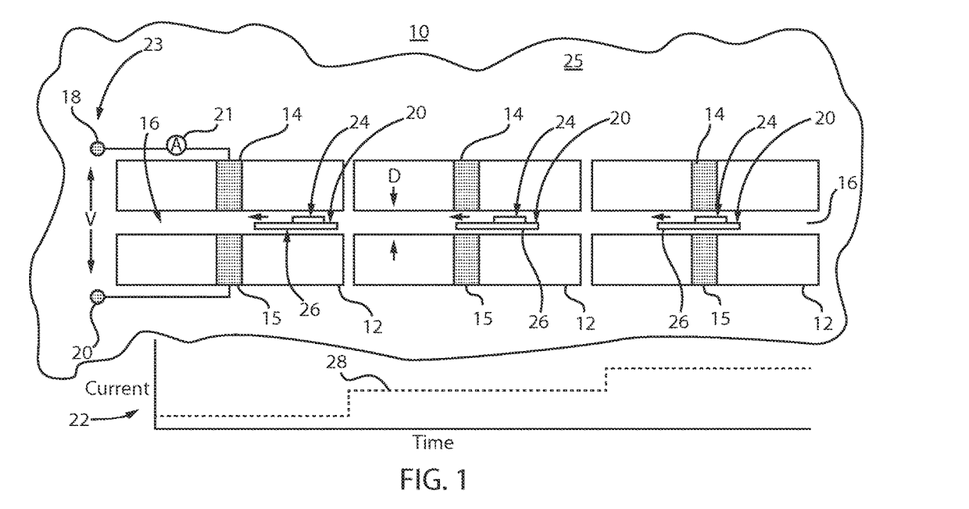
FIG. 1 is a cross-sectional view of a nanodevice showing sequence material moving in a nanochannel in accordance with the present principles.

Referring now to the drawings in which like numerals represent the same or similar elements and initially to FIG. 1, a nanodevice (sequence reader) 10 is shown in accordance with one illustrative embodiment. The nanodevice 10 is referred to as such since the device 10 includes a nanochannel 16 for transporting genetic material to be evaluated; however, microchannel (micron sized (e.g., 1-100 microns) devices are also contemplated. In one embodiment, the genetic material may include a DNA molecule 26 (single stranded (ss) DNA (ssDNA), double stranded (ds) DNA (dsDNA), etc.) after a probe molecule 24 functionalization to bind the molecule 26 with the probe molecule 24. A functionalized molecule 20 includes the combined probe molecule 24 and the DNA molecule 26. The functionalized molecule 20 is threaded into the nanochannel(s) 16 where the molecule 20 is linearized.

Sections 12 may be formed on a substrate 25, e.g., Si, glass, etc., by depositing and patterning a dielectric material, e.g., a silicon oxide or silicon nitride. Electrodes 14, may be formed by depositing a conductive layer over the dielectric material to fill in spaces between mid-regions of the dielectric sections 12 and polishing away the excess of conductive materials using a Chemical Mechanical Polishing (CMP) process. This structure of a conductive strip embedded within dielectrics can also be fabricated by depositing and pattern etching conductive strips (electrodes 14, 15), and then overcasting section 12 with dielectric materials, e.g., silicon oxide or silicon nitride. Subsequently, the dielectrics are polished with CMP until the conductive strip(s) (electrodes 14, 15) is/are exposed. It may be necessary to design a filling structure, e.g., micro- or nano-pillar arrays of the conducting materials, to support the polishing in the later case. After the formation of sections 12 and electrodes 14, 15, an etching process may be performed to form the nanochannel 16 through the center of the electrodes 14, 15 to expose the electrodes 14, 15 inside the channel. On the other hand, a channel can also be etched through electrodes 14 or 15 to split the conductive portions into two electrodes (see e.g., FIG. 7), e.g., transverse to the nanochannel 16. A dielectric top layer (not shown) may be formed over the nanochannel 16 in later steps to provide a closed nanochannel, for example, by plasma enhanced chemical vapor deposition (PECVD) of silicon oxide, silicon nitride, etc. or sputtered dielectric materials.

Other processing methods and materials may be employed to create the nanodevice 10, e.g., by wafer bonding a flat wafer or glass slides. In this process, the bonding is realized by thermally annealing two firmly pressed surfaces, e.g., a CMP polished oxide surface that has been pretreated with $O_2$ plasma or a piranha solution. Silicon-oxygen-silicon bonds will be formed at high annealing temperatures, e.g., greater than 400 degrees C., or hydrogen bonding will be formed under lower temperatures less than 200 degrees C.

Electrodes 14, 15 are exposed inside the nanochannel 16. In this embodiment, the electrodes 14, 15 are arranged face to face across the channel 16 so that a tunneling current from one electrode 14 can interact with the molecule 20 inside the channel 16 and be accepted by the counter electrode 15 (on an opposite side of the channel 16). The electrodes 14, 15 may include, e.g., $TiN_x$, Pd, Au or other metals. With a fixed electrode distance D, single strand DNA and double strand DNA can show different tunneling currents. With an additional mark molecule, the tunneling current difference between binding sequence and non-binding sequencing can be larger. The DNA molecule is immersed in a fluid and is preferably driven through the nanochannel by electrophoresis forces with applied electrical potential at the two ends of the channel 16. This can be implemented using electrodes (not shown) at each end of the nanodevice 10.

The channel length can be from about 10 nm up to about 100 microns, with an average channel width or diameter of about 10 nm to about 1 micron. If no additional mark molecule is attached to the DNA, the narrowest portion of the channel, e.g., the distance D between surfaces of electrodes 14 and 15 should be in the range of, e.g., about 1 to 3 nm to differentiate the tunneling current between single strand DNA and double strand DNA.

The surfaces of electrodes 14 and 15 can be functioned with organic molecules which can interact differently between binding strands and non-binding strands, for example, differentiate the single strand DNA and double strand DNA, and therefore, enhance the tunneling current difference.

The device 10 may be separated into segments 12. Each segment may include its own electrodes 14, 15. While the electrodes 14, 15 are powered by a voltage (V) (power circuit 23) shown across nodes 18 and 20 of the left-most segment 12, the nodes 18 and 20 can be connected across the other electrode pairs 14, 15 for the other segments 12 as well or each segment may have its own power circuit 23 and sensor 21 (e.g., current sensor).

When the DNA is passing the gap between two tunneling electrodes 14, 15, a time fly curve 22 shows when the probe sequence 24 is passing the electrodes 14, 15. From the time fly current signal 28, a position of the probe sequence 24 on the entire sequence 20 can be estimated.

Figure 2:
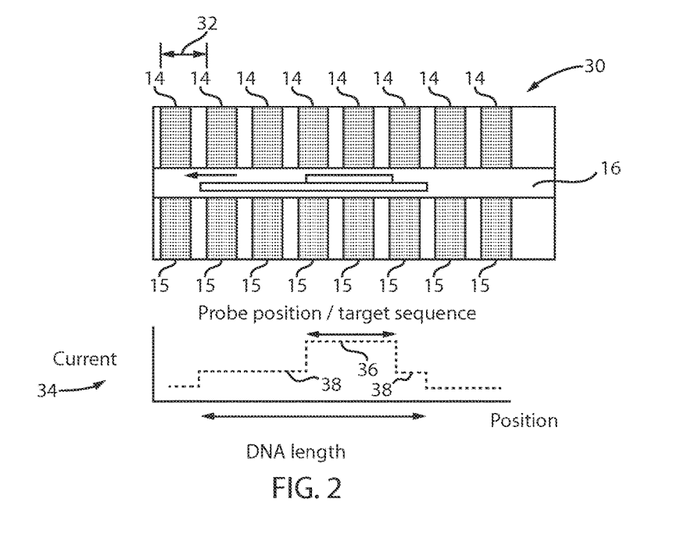
FIG. 2 is a cross-sectional view of a nanodevice formed as an array of electrodes in accordance with the present principles.

Referring to FIG. 2, an array of tunneling electrodes 30 can be fabricated along a nanochannel 16. A position of the electrode 14, 15 becomes a distance mark. A pitch or spacing 32 between pairs of electrodes 14, 15 of the array 30 may be selected to provide a fine enough grid such that the position of the target probe 24 can be found precisely by comparing a current readout 34 along the electrodes of the array 30. The current readout 34 includes a portion 36 indicating the target probe 24, and a portion 38 indicating the DNA molecule 26.

Optical mapping of genetic material typically employs a fluorescence probe to map the target sequencing. Instead of using a fluorescence probe and optical microscope to visualize the probe, the present principles employ a non-fluorescence probe molecule for sequence reading. The probe molecule can be, e.g., a single strand DNA without functionalization, a DNA functionalized with a conductive organic molecule or nanoparticles, etc. As described, the present embodiments detect an electrical signal which is a tunneling resistance/barrier across a channel through a target DNA molecule. The tunneling barrier/resistance can change when the probe molecule passes the tunneling electrode, thus providing a measuring signal.

Compared with optical mapping, some advantages of the tunneling electrode mapping in accordance with the present principles, include that the tunneling electrode mapping: 1) does not require a fluorescence mark on the probe—fluorescence marking is usually more expensive than a probe without a fluorescence mark or with less expensive conductive organic or nanoparticle marks; 2) does not require an optical microscope, detection circuits for the nanodevice can be monolithically integrated on a chip, no external microscope/tools are required for the data read out, therefore having a lower price; 3) high resolution is provided, which is not limited by the optical resolution limit from the fluorescence microscope; and 4) fast data processing is achieved, due at least in part to the signal being electrical, which can be directly feed to a computational processor; thus, there is no need for optical-electrical signal conversion which can be a burden for optical mapping.

Figure 3:
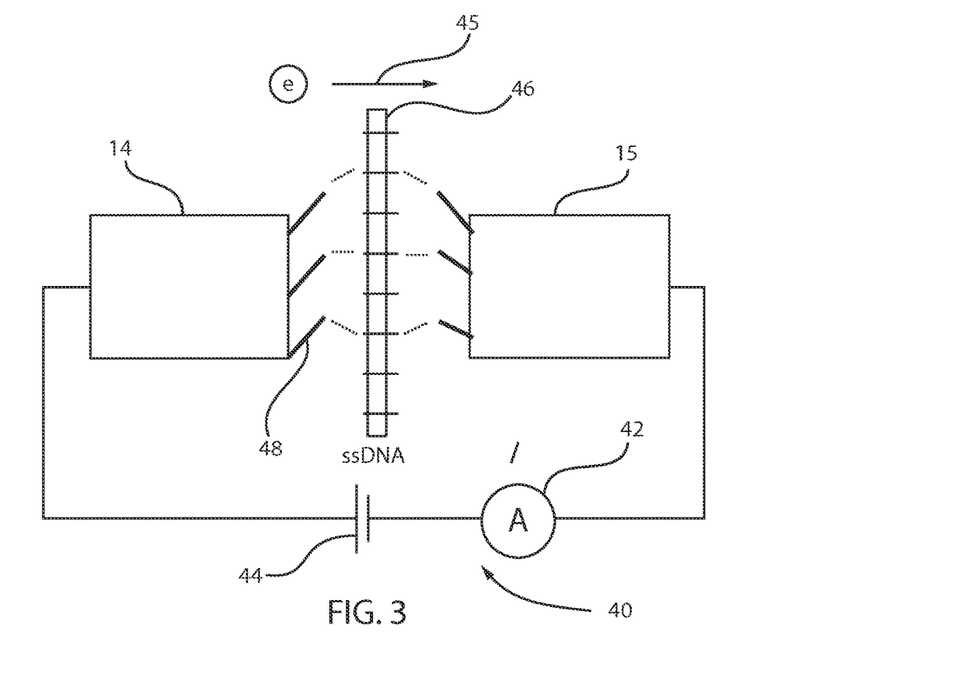
FIG. 3 is a cross-sectional view of a nanodevice showing a single stranded molecule being passed through a nanochannel in accordance with the present principles.
Figure 4:
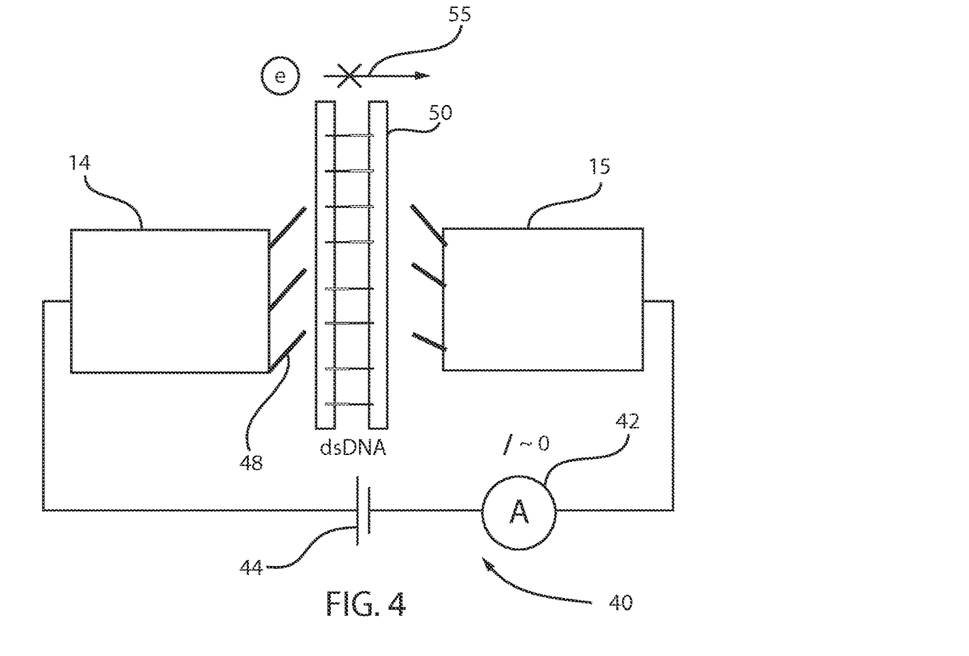
FIG. 4 is a cross-sectional view of a nanodevice showing a double stranded molecule being passed through a nanochannel in accordance with the present principles.

Referring to FIGS. 3 and 4, a device/process for a nanodevice in accordance the present principles includes distinguishing dsDNA and ssDNA by molecular interaction. Electrodes 14, 15 are connected to a power circuit 40, which includes a power source 44 and functions as a current sensor 42 to provide tunneling current across the electrodes 14, 15. In FIG. 3, exposed surfaces of the electrodes 14, 15 can be coated with self-assembled molecules 48 with a functional head-group such as, e.g., benzamide and/or imidazole. The head group can interact with unpaired bases (H-bonds) of ssDNA 46, producing a burst of tunneling current 45. In FIG. 4, dsDNA 50 has no unpaired bases; therefore it cannot interact with the head group, resulting in much less tunneling current 55. Measuring the tunneling current (I), the presence of a strand can be detected, and the type of strand (dsDNA or ssDNA) can be determined.

Figure 5:
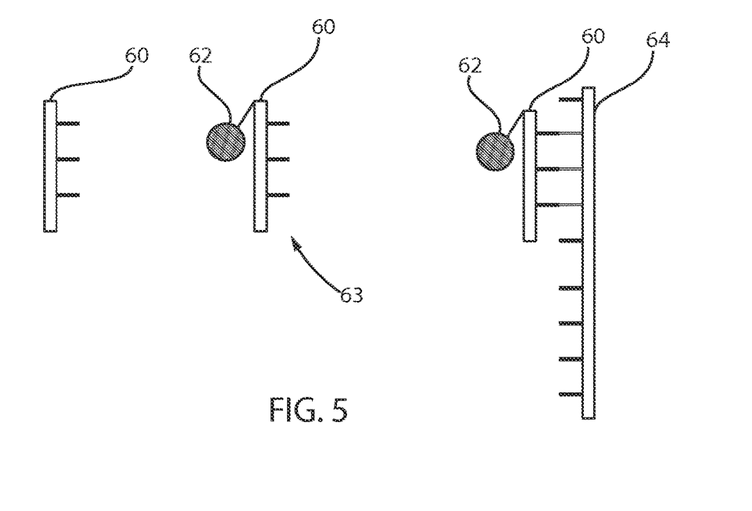
FIG. 5 is a diagram showing stages for mounting a probe and a conductive particle on a target sequence.
Figure 6:
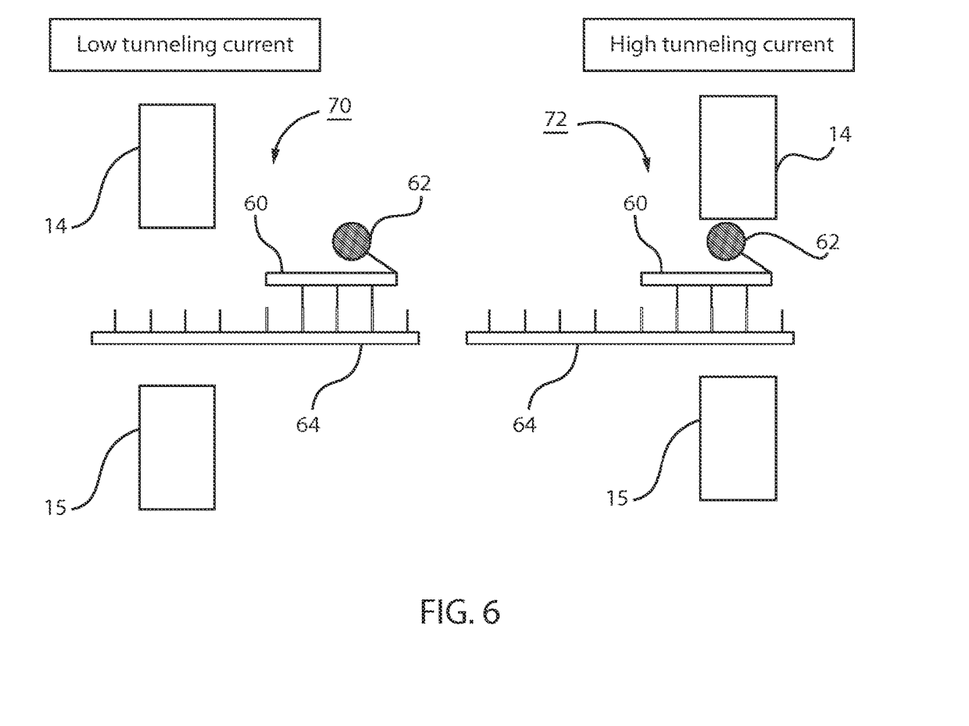
FIG. 6 is a cross-sectional view of a nanodevice showing the target device of FIG. 5 being analyzed in a low tunneling current scenario and a high tunneling current scenario in accordance with the present principles.

Referring to FIGS. 5 and 6, a device/process for a nanodevice in accordance the present principles includes distinguishing dsDNA and ssDNA by functional prober sequencing. In FIG. 5, a probe ssDNA 60 can be functionalized with a metal nanoparticle, conducting molecule or polymer 62 to form a functionalized prober molecule 63. The functionalized prober molecule 63 is bonded to a targeted sequence 64. In FIG. 6, the targeted sequence 64 can be distinguished by a high tunneling current signal through the conducting particle/molecule 62 between electrodes 14 and 15. The electrode surface can be functionalized to increase the interaction with the metal particle/conducting molecule 62 in a high tunneling current scenario 72 over a low tunneling current scenario 70, which the conducting particle/molecule 62 has not yet entered (or has already passed) between the electrodes 14, 15.

Figure 7:
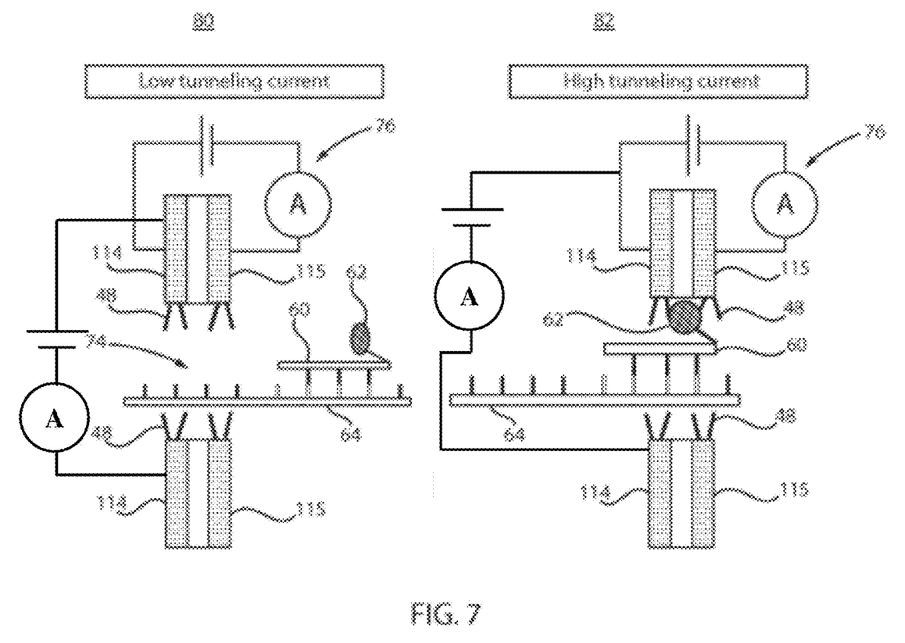
FIG. 7 is a cross-sectional view of a nanodevice showing electrodes on a same side of the nanochannel and the target device of FIG. 5 being analyzed in a low tunneling current scenario and a high tunneling current scenario in accordance with the present principles.

Referring to FIG. 7, another device/process for a nanodevice in accordance with the present principles includes distinguishing dsDNA and ssDNA by functional prober sequencing. A probe(s) ssDNA 60 can be functionalized with metal nanoparticles, conducting molecule or polymer 62 as depicted in FIG. 5, and the functionalized prober molecule 63 is bonded to the targeted sequence 64. In addition, exposed surfaces of electrodes 114, 115 can be coated with self-assembled molecules 48 with a functional head-group such as, e.g., benzamide and/or imidazole. The head group can interact with unpaired bases of in region 74 of the ssDNA 64, producing a burst of tunneling current across the channel between electrodes 114 (an electrode 115) on opposite side of the channel (across the region 74) in scenario 80.

In addition to or instead of the across the channel current monitoring, a power circuit 76 includes a potential across electrodes 114 and 115 on a same side of the channel (same side of the ssDNA). When the conducting particle/molecule 62 is engaged by molecule 48, the targeted sequence 64 can be distinguished by a high tunneling current signal through the conducting particle/molecule 62 in scenario 82. The current through the particle/molecule 62 occurs on a same side of the target sequence 64 in scenario 82 as opposed to the low tunneling current determined through the circuit 76 in the scenario 80 when the particle cannot cause conduction between electrodes 114 and 115.

Figure 8:
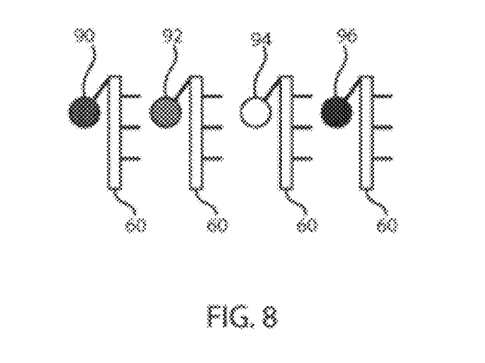
FIG. 8 is a diagram showing the mounting a different conductive particle types in accordance with the present principles.
Figure 9:
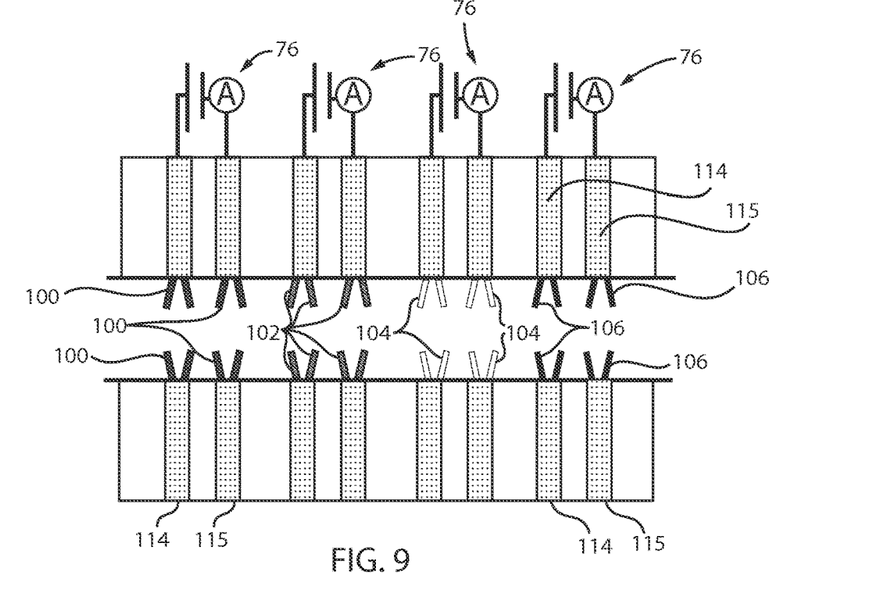
FIG. 9 is a cross-sectional view of a nanodevice having electrode sets coated with self-assembled molecules corresponding with the different conductive particle types in accordance with the present principles.
Figure 10:
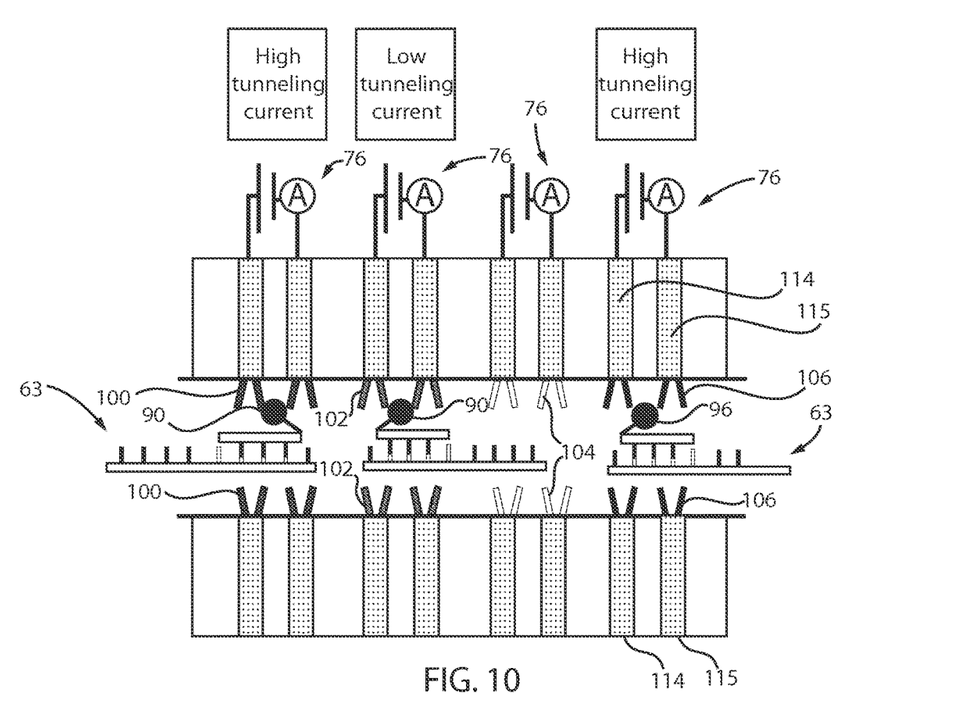
FIG. 10 is a cross-sectional view of the nanodevice of FIG. 9 showing electrical responses to same and different combinations of self-assembled molecules and different conductive particle types in accordance with the present principles.

Referring to FIGS. 8, 9 and 10, a nanodevice and method in accordance the present principles includes multiple probe detections. In FIG. 8, a plurality of probes 60 are functionalized with conductive particles/molecules 90, 92, 94, and 96. While four particle/molecules are depicted it should be understood that a greater or lesser number may be employed.

In FIG. 9, a series of stacked electrodes 114, 115 are assembled in the same manner as in FIG. 7. In this embodiment, each electrode pair 114 and 115 includes a different type of self-assembled molecules 100, 102, 104 and 106. Each of self-assembled molecules 100, 102, 104 and 106 are formed on the electrodes 114 and 115 as shown in FIG. 9.

In FIG. 10 with continued reference to FIGS. 8 and 9, the self-assembled molecules 100, 102, 104 and 106 correspond with a type of conductive particles/molecules 90, 92, 94, and 96 such that when the conductive particles/molecules 90, 92, 94, and 96 engage the corresponding self-assembled molecules 100, 102, 104 and 106, a high tunneling current is measured. When the conductive particles/molecules 90, 92, 94, and 96 engage non-corresponding self-assembled molecules 100, 102, 104 and 106, a low tunneling current is measured. In other words, functionalized nanoparticles 90, 92, 94, and 96 bind to the specific molecules 100, 102, 104 and 106 that the channel electrodes are functionalized with.

In one example as depicted in FIG. 10, particle 90 provides a high tunneling current for circuit 76 when the particle 90 encounters the self-assembled molecules 100 and provides low tunneling current when engaged with self-assembled molecules 102, 104 and 106. In one example as depicted in FIG. 10, particle 96 provides a high tunneling current for circuit 76 when the particle 96 encounters the self-assembled molecules 106. Low tunneling current would be provided when particle 96 engages with self-assembled molecules 100, 102 and 104.

Conductive molecules 100, 102, 104 and 106 may include polymers such as, e.g., polyacetylene, polypyrrole, etc. Conductive particles 90, 92, 94, and 96 may include, e.g., gold, silver, copper or other nanoparticles. The molecules 100, 102, 104 and 106 and particles 90, 92, 94, and 96 are respectively configured to yield a high current for only their mated or matching set. This may be achieved by manipulating sizes and materials for the molecules and particles.

Figure 11:
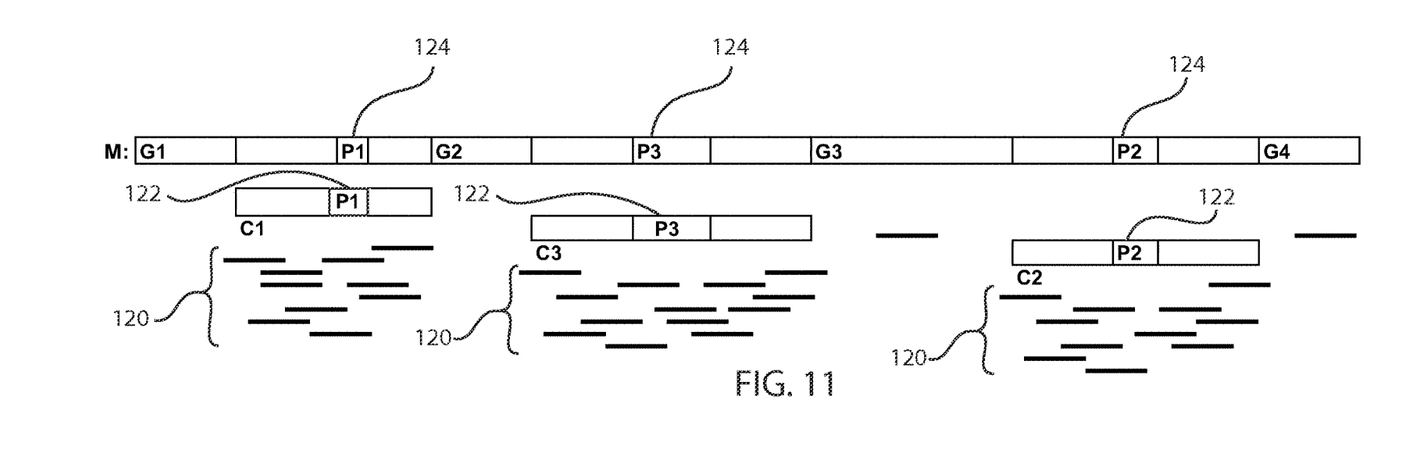
FIG. 11 is a schematic diagram showing a genome assembly application in accordance with the present principles.

Referring to FIG. 11, a genome assembly finishing application is shown in accordance with the present principles. A short-read sequencing and assembly generally yields a set of scaffolds, whose order on the genome is unknown. Probes are designed on the scaffold sequence to infer their order and lengths of gaps between them. This technology can replace the current alternative, expensive and labor-intensive physical map construction. For this application, it will be necessary to detect probes 122 of different types by employing the nanodevices described herein.

In the example shown in FIG. 11, contigs $C_1$, $C_2$, $C_3$ are assembled from next-generation sequencing (NGS) reads 120. In many instances, there is not enough read coverage to connect the contigs. Lengths of probes 122 are $|P_1|<|P_2|<|P_3|$. The probes 122 are attached to a reference molecule M (here M is processed starting from the left). A double stranded DNA on M (blocks 124) is employed to recognize and label probes 122. First, $P_1$ is observed then $P_3$ and finally $P_2$, the order of contigs 120 in sequence S of molecule M is $<C_1, C_3, C_2>$. Distances between probes 122 are used to infer sizes of gaps G1, G2, G3, G4, etc. before, between, and after contigs 120.

The genome assembly finishing application may be stated as follows.

Input:

N in silico contig sequences $C_1, C_2, \ldots, C_N$ have been determined (e.g., by assembling NGS data) for a single stranded DNA molecule M.

Problem:

Order and align N contigs to reflect sequence S of DNA molecule M

Solution:

Design synthetic DNA probe sequences $P_i$ 122 in such a way that they are complementary to regions $C_1, C_2, \ldots, C_N$ and hybridize to the single stranded molecule M, the probes 122 having either different lengths or being tagged with labels to distinguish between different probe sequences. Applied technology will recognize the order and distances between the probes 122.

In one embodiment, the protocol may include designing a probe $P_i$ complementary to one region of each contig $C_i$, $P_i$ sequence, which is present in $C_i$ and not in $C_j$ for all $j=1, \ldots, N$, $j \neq i$. DNA probes P 122 are manufactured and attached to DNA molecule M. Next, an order of probes 122 on M is recognized (e.g., from the length of double-stranded DNA using the nanodevices in accordance with the present principles).

Distances between probes 122 on M is recognized (e.g. from observed timing between double-stranded DNA using the nanodevices in accordance with the present principles). A sequence S of molecule M is inferred as a combination of contigs C and gaps G.

Figure 12:
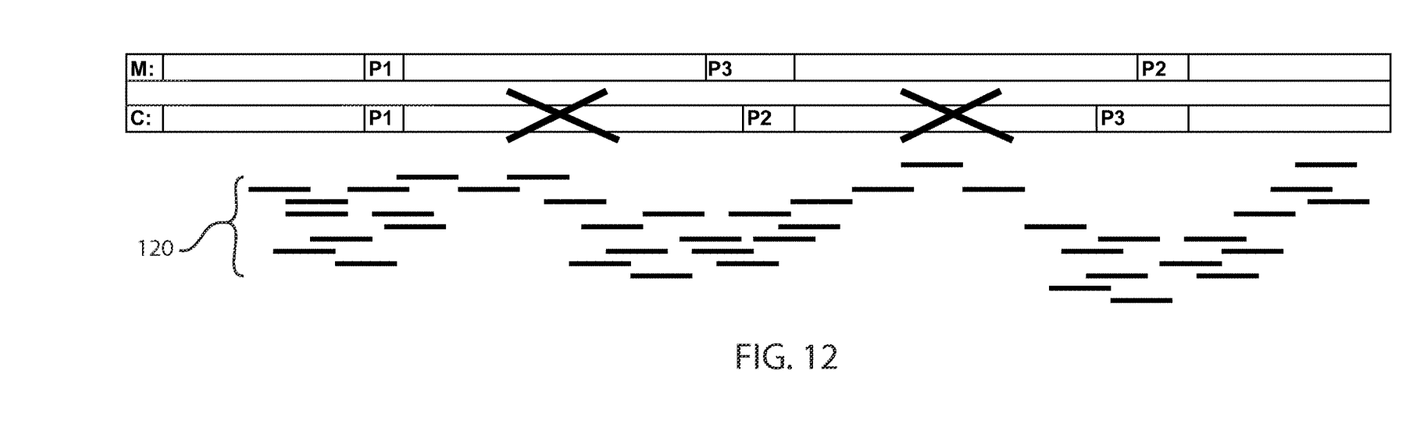
FIG. 12 is a schematic diagram showing a sequence validation application in accordance with the present principles.

Referring to FIG. 12, a sequence validation application is shown in accordance with the present principles. When a number of alternative hypotheses for a final genome assembly exists, probes can be designed to distinguish between the assemblies. For example, each run contains a set of probes specific to an assembly, and the binding or non-binding of those probes on the target molecule M indicates a correct or incorrect assembly.

Contig C is assembled from NGS reads 120. The regions between probes 122 have low sequencing coverage, and the correctness of the sequence C needs to be validated. First, $P_1$ is observed then $P_3$ and finally $P_2$. The order of the sequences surrounding $P_2$ and $P_3$ are reversed on contig C in FIG. 12. An assembly error is detected in C between probes $P_1$ and $P_2$. Timing between $P_1$ and $P_3$ suggests the true distance between $P_1$ and $P_3$ on molecule M. Timing can be measured using a nanodevice in accordance with the present principles. The process may be iterated to validate the sequence C with increasing resolution.

The sequence validation application may be stated as follows.

Input:

In silico contig sequence C that has been determined (e.g., by assembling NGS data); single stranded DNA molecule M Problem:

Validate that C matches sequence S of DNA molecule M

Solution:

Design synthetic DNA probe sequences P in such a way that they are complementary to unique subsequences in C and hybridize to single stranded molecule M, the probes having either different lengths or being tagged with labels to distinguish between different probe sequences. Applied technology will recognize the order and distances between probes.

In one embodiment, the protocol may include the following. Probes $P_i$ 122 are designed complementary to unique subsequences in contig C. DNA probes P 122 are manufactured and attached to DNA molecule M. An order of probes 122 on M is recognized (e.g., from length of double-stranded DNA). Distances between probes 122 are recognized on M (e.g., from observed timing between double-stranded DNA). Sequence C is validated by comparing the location of probes P 122 on molecule M.

For the above applications and others, when the DNA molecule is short enough to pass through the nanodevice without breaking, the time it takes to pass through the device is an indication of a total molecule size. The process can be repeated on the same molecule or different copies of the same molecule for a more accurate estimate. Estimating a total sequence length or lengths between probes or any other features by passing the sequence through a nanodevice in accordance with the present principles is referred to herein as "timing".

If the probes will not bind to a sequence with single nucleotide changes, the present nanodevice technology can be used to detect the presence/absence of sequence variants at specific target regions (e.g., identifying sequence polymorphisms). The nanodevices as described herein can be utilized to detect the presence of known genome sequences by appropriate probe designs. It can also be used to identify the absence of a known genome sequence as regions where no fragments from the sample bind (e.g., identifying the presence or absence of DNA sequences).

For many applications accurate timing, i.e., time between probes or total molecule time, is needed information, as well as accurately transforming the time measurement into a base pair distance. For some applications, selective binding needing a 100% match between the probe and the target molecule is desired. For other applications, the ability to detect several types of probes in the same run is needed. Most applications listed are envisioned for short bacterial genomes, longer genomes, fragments of genomes, RNA or other sequences, etc.

Figure 13:
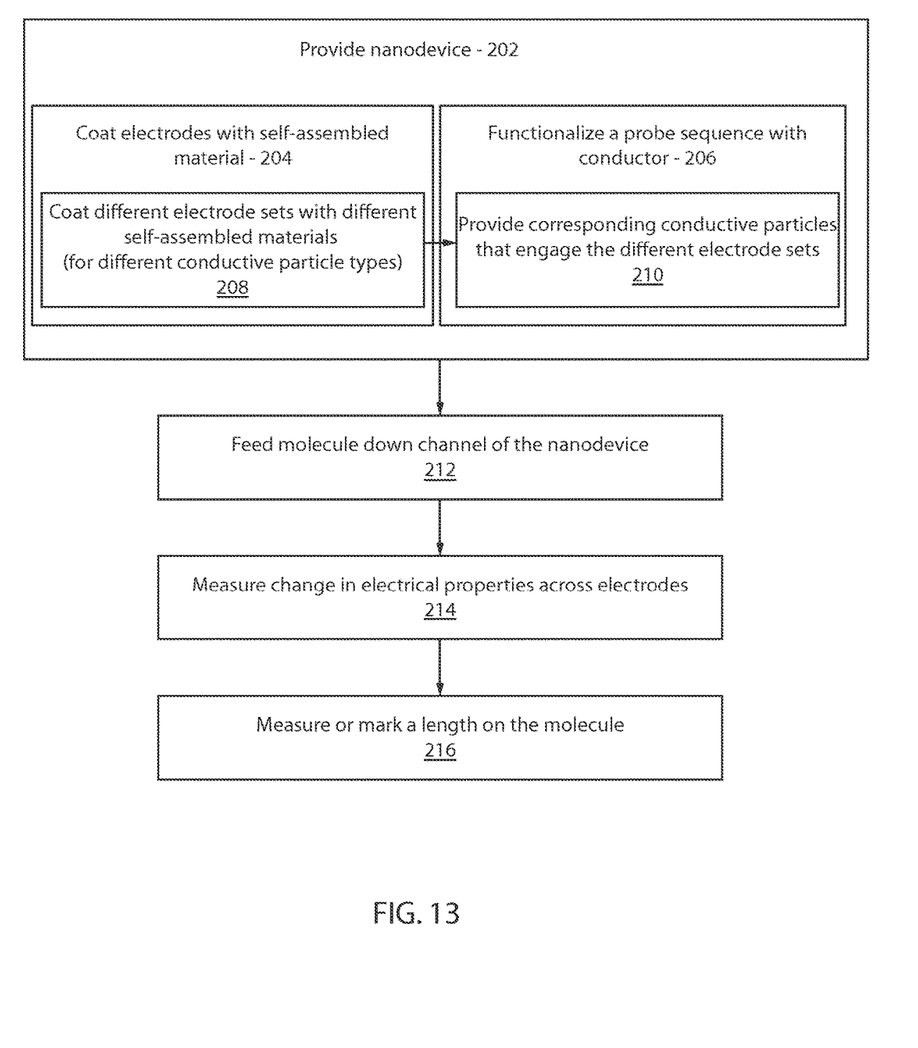
FIG. 13 is a block/flow diagram showing a method for analyzing a molecule in accordance with illustrative embodiments.

Referring to FIG. 13, a method for analyzing a molecule is illustratively shown. It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In block 202, a nanodevice is provided. The nanodevice includes a nanochannel disposed through a dielectric material, which is formed on a substrate. A first electrode is formed within the dielectric material and has a surface exposed within the nanochannel. A second electrode is formed within the dielectric material and has a surface exposed within the nanochannel. Alternately, a conductor may be patterned on the substrate, then buried in dielectric material and polished to form the nanodevice. Other methods may also be employed, e.g., wafer transfer, etc.

A power circuit is connected between the first and second electrodes to create a potential difference between the first and second electrodes such that portions of a molecule can be identified by a change in electrical properties across the first and second electrodes. The electrodes may be together on one side of the nanochannel or may be disposed on opposite sides of the nanochannel. Other configurations are also possible and contemplated. Different configurations and embodiments may be employed depending on the application.

In block 204, the first and second electrodes may be coated with self-assembled molecules having a functional head-group. In block 206, a probe sequence is functionalized with a conducting molecule or particle to mark a position on the molecule. In block 208, in one embodiment, different sets of first and second electrodes are coated with a plurality of different functional molecules. In block 210, a plurality of conducting molecules or particle types is formed (functionalized). Each type corresponds to one of the different functional molecules, such that a type of conducting molecule or particle generates a different electrical response when between the first and second electrodes of its corresponding functional molecules (block 208) than any other first and second electrode having other functional molecules.

In block 212, a linearized version of the molecule is fed down the nanochannel such that the molecule passes between the first and second electrodes. The molecule may be immersed in fluid and the molecule may travel by supplying a pressure difference, employing a gravity flow, charging the molecule and subjecting the molecule to an electrical field, etc.

In block 214, the change in electrical properties across the first and second electrodes is measured as the molecule is disposed between the first and second electrodes to characterize the molecule or portions thereof. This may include measuring a difference in current flow, although other properties may be measured. For example, tunneling current generated when open strands are present between the first and second electrodes is higher than the tunneling current when closed stranded materials are present between the first and second electrodes. This may be employed to decipher ssDNA versus dsDNA or the like. Knowing properties of the sequences being analyzed, the currents may be correlated to physical properties of the target sequence, the probe, the conducting particles, etc.

In block 216, a length of the molecule or between portions of the molecule is measured. This can be employed to measure gaps in a sequence or to assist in assembling a sequence (e.g., the length of the molecule or portions may be employed in one of genome assembly finishing and/or sequence validation).

Having described preferred embodiments for tunneling junction to distinguish targeted DNA segment for DNA sequence assembly (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A nanodevice, comprising:
a nanochannel disposed through a dielectric material;
a first electrode on a first side of the nanochannel formed within the dielectric material and having a surface exposed within the nanochannel, wherein the first electrode comprises a metal;
a second electrode on a second side of the nanochannel formed within the dielectric material and having a surface exposed within the nanochannel opposite the first electrode, wherein the second electrode comprises a metal;
a third electrode on the first side of the nanochannel formed within the dielectric material and having a surface exposed within the nanochannel, wherein the third electrode comprises a metal;
a fourth electrode on the second side of the nanochannel formed within the dielectric material and having a surface exposed within the nanochannel opposite the third electrode, wherein the fourth electrode comprises a metal;
a set of opposing electrodes including the first electrode and the second electrode;
at least one set of adjacent electrodes, a first set including the first electrode and the third electrode, and wherein each set of adjacent electrodes is parallel to and laterally separated from any other set of adjacent electrodes on a same side of the nanochannel;
a first power circuit connected between the set of opposing electrodes to create a potential difference between the first electrode and the second electrode such that a molecule in the nanochannel between the at least one set of opposing electrodes modifies the potential difference between the at least one set of opposing electrodes; and
a second power circuit connected between the set of adjacent electrodes to create a potential difference between the first electrode and the third electrode such that the molecule in the nanochannel between the at least one set of adjacent electrodes modifies the potential difference between the at least one set of adjacent electrodes.

2. The nanodevice as recited in claim 1, wherein the at least one set of opposing electrodes generate a tunneling current in response to open strands being present between the at least one set of opposing electrodes.

3. The nanodevice as recited in claim 1, wherein the at least one set of opposing electrodes generate a reduced tunneling current in response to closed stranded materials being present between the at least one set of opposing electrodes.

4. The nanodevice as recited in claim 1, wherein the spacing of the at least one set of adjacent electrodes relative to one another is configured to measure length for genome assembly finishing and/or sequence validation.

5. The nanodevice as recited in claim 1, wherein the nanodevice includes an array of electrodes disposed along the length of the nanochannel.

6. The nanodevice as recited in claim 1, wherein the nanodevice includes a plurality of sections having the nanochannel running through the plurality of sections, each section having a set of opposing electrodes disposed across the nanochannel.

7. A nanodevice, comprising:
a nanochannel disposed through a dielectric material;
a first electrode on a first side of the nanochannel formed within the dielectric material and having a surface exposed within the nanochannel, wherein the first electrode comprises a metal;
a second electrode on a second side of the nanochannel formed within the dielectric material and having a surface exposed within the nanochannel opposite the first electrode, wherein the second electrode comprises a metal;
a third electrode on the first side of the nanochannel formed within the dielectric material and having a surface exposed within the nanochannel, wherein the third electrode comprises a metal;
a fourth electrode on a second side of the nanochannel formed within the dielectric material and having a surface exposed within the nanochannel opposite the third electrode, wherein the fourth electrode comprises a metal;
a set of opposing electrodes including the first electrode and the second electrode;
a set of adjacent electrodes including the first electrode and the third electrode;
a first power circuit connected between the set of opposing electrodes to create a potential difference between the first electrode and the second electrode such that a molecule in the nanochannel between the at least one set of opposing electrodes modifies the potential difference between the at least one set of opposing electrodes;
a second power circuit connected between the set of adjacent electrodes to create a potential difference between the first electrode and the third electrode such that the molecule in the nanochannel between the at least one set of adjacent electrodes modifies the potential difference between the at least one set of adjacent electrodes; and
a DNA sequence functionalized with a conducting particle, the conducting particle configured to mark a portion of the molecule such that in response to the conducting particle being between at least one of the set of opposing electrodes and the set of adjacent electrodes, a change in the electrical properties occurs, the at least one of the set of opposing electrodes and the set of adjacent electrodes being coated with self-assembled molecules having a functional head-group.

8. The nanodevice as recited in claim 7, wherein the at least one set of opposing electrodes generate a tunneling current in response to open strands being present between the at least one set of opposing.

9. The nanodevice as recited in claim 7, wherein the at least one set of opposing electrodes generate a reduced tunneling current in response to closed stranded materials being present between the at least one set of opposing electrodes.

10. The nanodevice as recited in claim 7, wherein the spacing of the at least one set of adjacent electrodes relative to one another is configured to measure length for genome assembly finishing and/or sequence validation.

11. The nanodevice as recited in claim 7, wherein the nanodevice includes an array of electrodes disposed along the length of the nanochannel.

12. The nanodevice as recited in claim 7, wherein the nanodevice includes a plurality of sections having the nanochannel running through the plurality of sections, each section having a set of opposing electrodes disposed across the nanochannel.

13. The nanodevice as recited in claim 7, wherein the at least one set of adjacent electrodes generate a tunneling current when a conducting particle or molecule is present between or near the at least one set of adjacent electrodes.

14. The nanodevice as recited in claim 7, wherein the at least one set of adjacent electrodes generate a reduced tunneling current when a conducting particle or molecule present is not compatible with the self-assembled molecules on the at least one set of adjacent electrodes.

15. The nanodevice as recited in claim 7, wherein the spacing of the at least one set of adjacent electrodes relative to one another is configured to measure at least one of lengths between portions of the molecule and a length of the molecule.

16. The nanodevice as recited in claim 15, wherein the spacing of the at least one set of adjacent electrodes relative to one another is configured to measure length for genome assembly finishing and/or sequence validation.

17. The nanodevice as recited in claim 7, wherein the nanodevice includes an array of electrodes disposed on two sides of the nanochannel.

18. The nanodevice as recited in claim 7, wherein the nanodevice includes:
   a plurality of different functional molecules, each being coated on a different set of the at least one set of adjacent electrodes; and
   a plurality of conducting molecules or particle types, each type corresponding to one of the different functional molecules, such that a type of conducting particle generates a different electrical response when between the at least one set of adjacent electrodes of its corresponding functional molecules than any other of the at least one set of adjacent electrodes having other functional molecules.

19. The nanodevice as recited in claim 7, wherein a probe sequence comprises a DNA sequence.

* * * * *